United States Patent [19]

Koizumi et al.

[11] Patent Number: 4,468,121

[45] Date of Patent: Aug. 28, 1984

[54] SPECTROPHOTOMETRIC ANALYZER HAVING DUAL MONOCHROMATORS

[75] Inventors: Hideaki Koizumi, Tokyo; Konosuke Oishi, Mito, both of Japan

[73] Assignee: Hitachi, Ltd., Tokyo, Japan

[21] Appl. No.: 361,381

[22] Filed: Mar. 24, 1982

[30] Foreign Application Priority Data

Mar. 31, 1981 [JP] Japan .................................. 56-46462

[51] Int. Cl.³ .............................................. G01J 3/18
[52] U.S. Cl. .................................... 356/328; 356/333; 356/334
[58] Field of Search ................. 356/326, 328, 331–334

[56] References Cited

U.S. PATENT DOCUMENTS 3,521,960  7/1970  Newcomer ........................... 356/333
3,936,191  2/1976  Chupp ................................... 356/333

FOREIGN PATENT DOCUMENTS 54-163987 11/1979 Japan .

Primary Examiner—F. L. Evans
Attorney, Agent, or Firm—Antonelli, Terry & Wands

[57] ABSTRACT

A spectrophotometric analyzer disclosed by this invention has two monochromators capable of operating independently of each other. In each monochromator, a light beam from a light source is made to be incident on an entrance slit, and, after dispersed and wavelength scanned, issued from an exit slit as an analyzed light beam. These analyzed light beams are detected by detectors. The entrance slits and the exit slits of the two monochromators are disposed rotation symmetrically. This can simplify the operation of switching between a series mode where the analyzed light from the exit slit of the one monochromator is made to be incident on the entrance slit of the other monochromator and a parallel mode where the both monochromators operate for detection independently from each other.

7 Claims, 8 Drawing Figures

F I G. 4
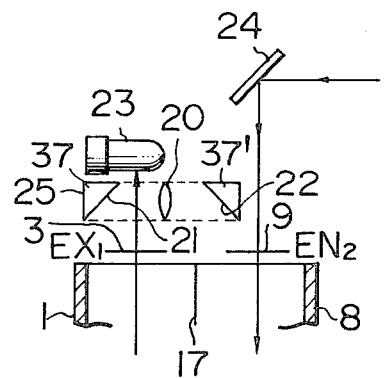
F I G. 5
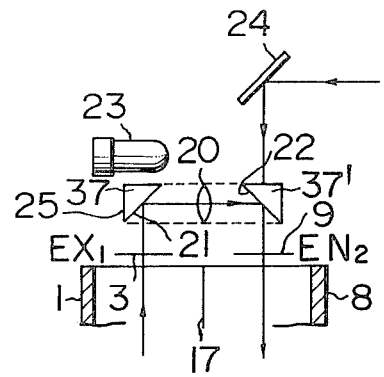
F I G. 6
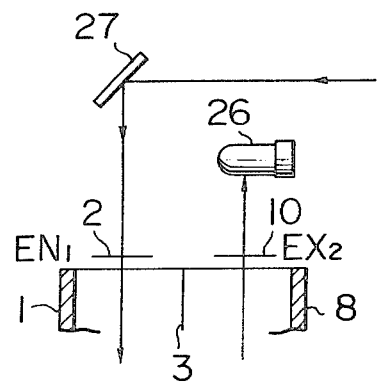

SPECTROPHOTOMETRIC ANALYZER HAVING DUAL MONOCHROMATORS

This invention relates to a spectrophotometric analyzer, and more particularly to a spectrophotometric analyzer suited to be used as an emission spectrochemical analyzer which ensures qualitative and quantitative analysis of metal from the emission spectrum of atoms.

In the conventional emission spectrochemical analysis, mainly 10 to 80 kinds of metal elements have been quantitatively analyzed by using ICP (inductively coupled plasma) or a d.c. arc as a light source and a polychromator or a monochromator as a spectrometer.

The polychrometer, in which a multiplicity of slits and detectors are arranged and fixed around a grating, has following merits and demerits.

Merits (1) Simultaneous analysis of many kinds of elements is possible (rapidly with a high S/N ratio).
(2) Internal standardization is possible.

Demerits (1) Due to the fixed slits, wavelength disprcrepancy happens due to a temperature variation.
(2) Due to a limitation on the space for the detectors, the number of measurable elements is restricted to 30 to 40.
(3) Any measurement of those elements outside the wavelengths preliminarily set is not possible.
(4) Use of a monochromator to eliminate the stray light is not possible.
(5) The apparatus is large in size and expensive.

On the other hand, the monochromator, in which a grating is rotated to scan the wavelength, has following merits and demerits.

Merits (1) There is no limit on the number of measurable elements.
(2) The state in the vicinity of an analytical line may also be measured.
(3) The apparatus is simple.
(4) Each analytical line can be measured under an optimum condition.
(5) The stray light can be eliminated by a prepositional monochromator.

Demerits (1) No simultaneous instantaneous measurement is possible.
(2) The time consumption for one measurement is long (due to scanning of the wavelength).

Recently, both the polychromator and the monochromator are used in substantially equal frequency.

Meanwhile, a dual wavelength spectrophotometer having two monochromators has been used in practice. Such a spectrophotometer, in which two monochromators are connected optically in series with each other so that they may be used as a double monochromator, is disclosed in Japanese Patent UM Application Kokai (Laid-Open) No. 163987/79. According to this spectrophotometer, such optical elements as entrance slits, output slits and gratings of the two monochromators are disposed in a plane symmetry. Thus, the switching between the dual wavelength method and the double monochromator method may be done by simultaneously tilting two mirrors which are constituted independently of each other to be capable of tilting. This requires a mechanism of moving the two mirrors in gang with each other. Furthermore, a mechanism of accurately setting the inclinations of the mirrors for each switching is necessary. Hence, a problem of complicating the switching mechanism will arise.

One objective of this invention is to provide a new spectrophotometric analyzer enjoying the merits of a polychromator while making a good use of the merits of a monochromator.

Another objective of this invention is to provide a spectrophotometric analyzer in which two independent monochromators are united to a most compact form and at the same time the two monochromators can be used either in parallel or in series by using a simple switching mechanism.

In one embodiment of this invention, when the monochromators are used in parallel, a light source is observed from two directions so that the light may be introduced into the two monochromators simultaneously. The wavelength is scanned in the two monochromators perfectly independently. Therefore, the measurement is performed without decreasing the S/N ratio while the measuring speed is increased to twice. The fact that the procession speed can be increased to twice has an important meaning.

The procession speed for the case of one monochromator is limited to measurement of 15 to 20 elements per one minute. If we assume that it takes one second to adjust the wavelength to the vicinity of one analytical line, 20 seconds would be needed for such adjust to 20 elements. In order to measure the 20 elements in one minute, the neighborhoods of 20 analytic lines should be slowly scanned in the 40 seconds left. Namely, a peak of each analytical line should be caught in scanning of a 5 Å wing in 2 seconds. If we assume that measurement proceeds in a step of 0.01 Å, data should be taken at 500 points in the scanning of 5 Å. This means that only a time of 0.002 second is allocated for each point. Although the above-mentioned procession speed is an upper limit for the case of scanning with one monochromator, processing at twice the speed can be attained without any problem if two monochromators are arranged in parallel and scanned independently with each other.

With application of two parallel monochromators, performance of the internal standardization which is a merit of the polychromator, becomes possible. Namely, a particular standard element may be continually observed in order to obtain a reference signal.

With a series arrangement of two monochromators, constitution of a double monochromator becomes possible. In this case, since the stray light which always causes a disturbance in the emission spectrochemical analysis can be removed, the detection limit can be decreased while the sensitivity as well as the accuracy can be increased.

As described above, by an appropriate usage of both parallel and series modes, the emission spectrochemical analysis can be done effectively. That is, when an unknown sample is to be analyzed, the whole wavelength range is scanned at first (screening) to obtain analytical lines of all elements. This screening process is a short time qualitative analysis, where two monochromators are disposed in a parallel mode. This increases the procession time.

The above process is indispensable for the analysis of all unknown samples. Especially, when the number of samples is large, it would be necessary that the process be done in as short time as possible. After this qualitative analysis is finished so that the general composition is grasped, one can decide a method of analysis. Next, the most suitable analytical line is selected for each element to be analyzed. For example, for iron (Fe) having a plurality of analytical lines, an analytical line with the highest sensitivity or with the least interference with other analytical lines is selected. In this case, it would be effective to enhance the sensitivity by arranging the two monochromators in series in the form of a double monochromator.

The arrangement which allows the use of two monochromators in the above-mentioned two modes together with the simple and secure switching method are important factors.

Above and other objectives and characteristics of this invention will be explained hereinafter with reference to the accompanying drawings.

FIGS. 4 and 5 are cross sectional views along a line IV—IV of FIG. 2 in two different states.

FIG. 6 is a cross sectional view along a line VI—VI of FIG. 2.

Figure 1:
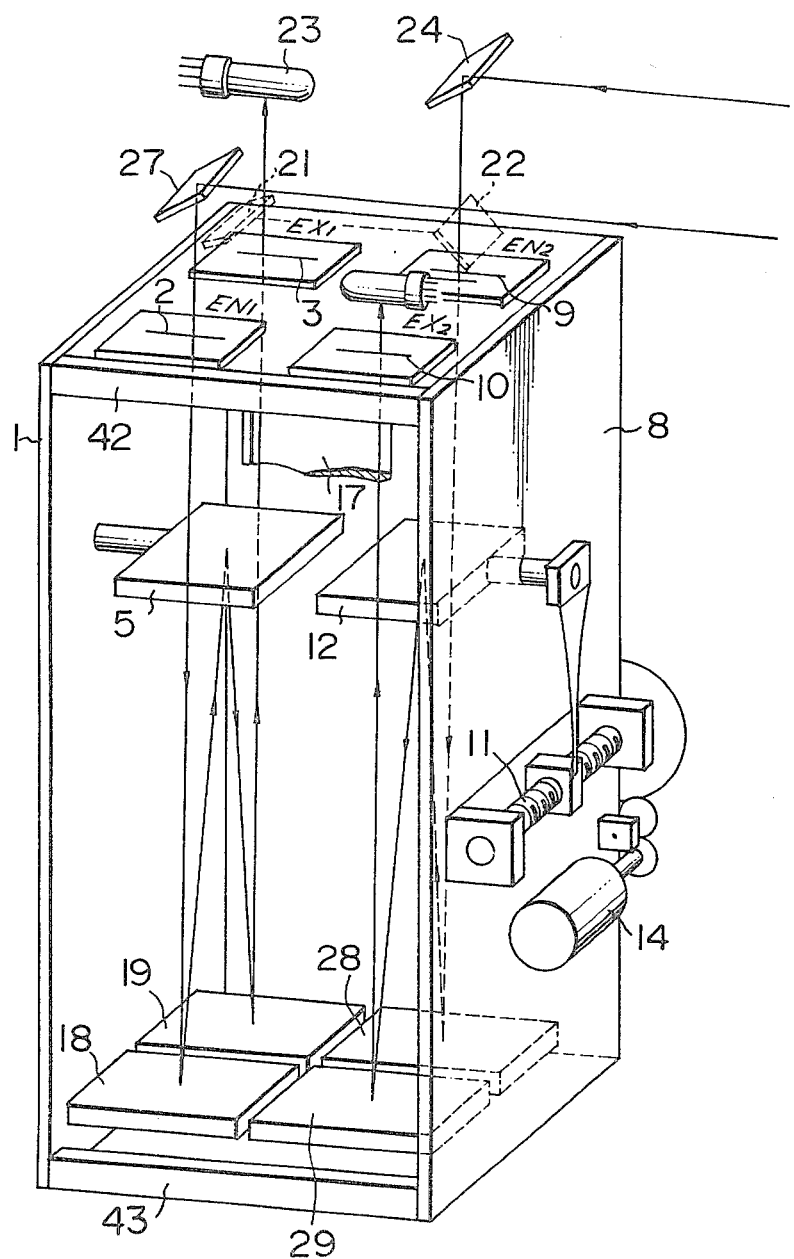
FIG. 1 is a schematic perspective view of a spectrophotometric analyzer without a top plate according to one embodiment of this invention.
Figure 3:
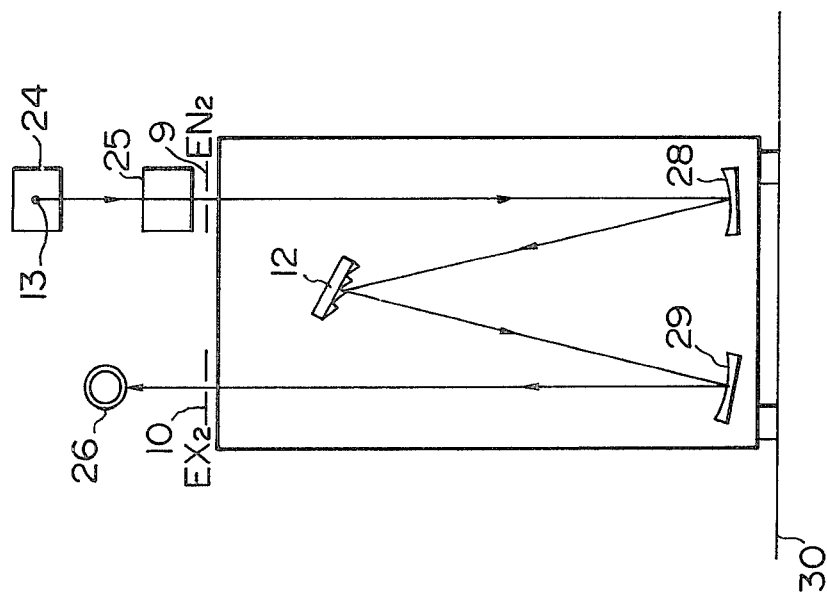
FIG. 3 is a cross sectional view along a line III—III of FIG. 2.
Figure 2:
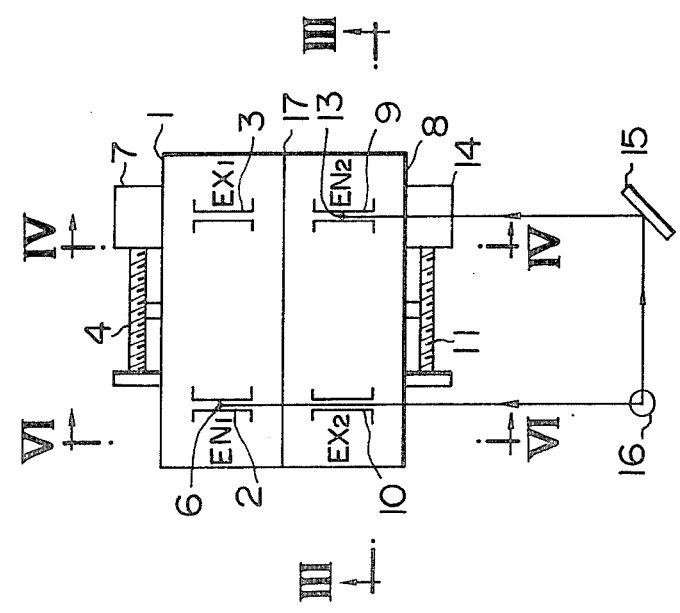
FIG. 2 is a planar view showing the positional relation between entrance slits and exit slits of two monochromators according to the embodiment as shown in FIG. 1.

In FIG. 1 through FIG. 6, two monochromators are disposed rotation symmetrically with respect to a longitudinal axis with a partition plate 17 therebetween. The first monochromator base 1 and the second monochromator base 8 are fixed to frame parts 42 and 43 so that two monochromators are united in one body. Transfer screws 4 and 11 are mounted outside the monochromator bases 1 and 8. One light beam emitted from a light source such as ICP is bent downwards by a right angle at an incident mirror 27 of the first monochromator and enters an entrance slit 2 of the same monochromator. The other light beam, after bent by a mirror 15, is bent downwards by a right angle at an incident mirror of the second monochromator and enters an entrance slit 9 of the second monochromator. This corresponds to the parallel mode as shown in FIG. 4.

In FIG. 1 through FIGS. 3, 5 and 12 denote gratings; 6 and 13 are points at which the light beams are bent by a right angle at mirrors 27 and 24 respectively; 7 and 14 denote driving mechanisms for the wavelength scanning containing pulse motors; 18, 19, 28 and 29 are collimator mirrors; and 23 and 26 denote detectors for the first and second monochromators, respectively.

In FIG. 5, the two monochromators are connected in series. Namely, when a slider 25 is moved laterally, the light beam coming out of the exit slit 3 of the first monochromator is reflected by mirrors 21 and 22 which are fixed to metal blocks 37 and 37' respectively, and then enters the entrance slit 9 of the second monochromator. The light beam 24 is interrupted by a top surface of the block 37'. A lens 20 focusses an image at the exit slit of the first monochromator onto the entrance slit 9 of the second monochromator. In this series mode, since the first monochromator functions as a prepositional monochromator, their entrance and exit slits may have a relatively large width. FIG. 6 shows neighborhoods of the entrance slit 2 of the first monochromator and of the exit slit 10 of the second monochromator. Around this section, nothing is placed for the series-parallel switching.

Figure 7:
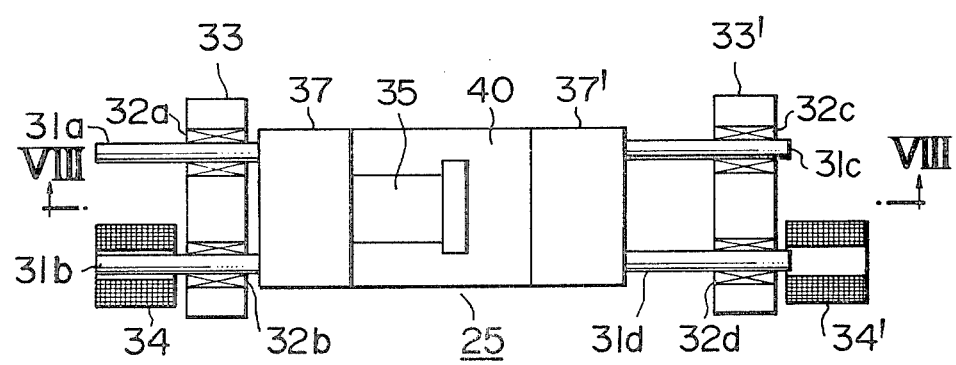
FIG. 7 is a planar view of a slider which is a main part of this invention.
Figure 8:
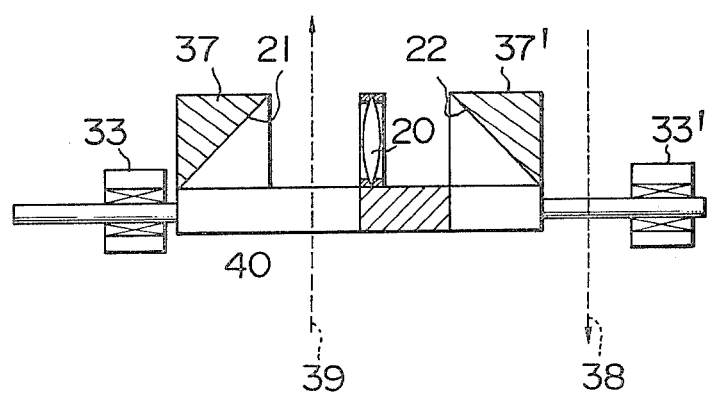
FIG. 8 is a cross sectional view along a line VIII—VIII of FIG. 7.

FIGS. 7 and 8 show detailed constitution of the parts of the slider 25 according to this embodiment. FIG. 7 is a planar view while FIG. 8 is a cross sectional view of FIG. 7 along a line VIII—VIII.

The slider 25 comprises reflection mirrors 21 and 22 fixed to mirror fixing blocks 37 and 37' respectively, a holder 40 holding the blocks 37 and 37' and having a light beam passing part 35, and slider rods 31a, 31b, 31c and 31d. The slider rods are mounted to fixed bases 33 and 33' having slide bearings 32a, 32b, 32c and 32d. In the presence of an indication signal for mode switch, an electromagnetic solenoid 34 or 34' is actuated to pull a slider rod (31b) or (31d) so that the reflection mirrors 21 and 22 change their positions. 38 and 39 denote incident and exit light beams, respectively.

As described above, since the entrance and exit slits of the two monochromators are disposed rotation symmetrically with respect to a center axis, switching between series and parallel modes of the two monochromators can be performed in a simple and secure fashion. Furthermore, as can be seen from FIGS. 1 and 2, since this arrangement has such a longitudinal constitution that both incident and exit light beams pass in vertical directions, mechanisms for wavelength scanning and other adjust parts can be mounted on side faces of easy treatment and maintenance. Further, the present arrangement is compact, requiring only a small set-up area.

If gratings with 1200 lines/mm and 2400 lines/mm are set in the first and second monochromators respectively, the measurable ranges of wavelength of the monochromators become 170 to 890 nm and 170 to 530 nm, respectively. Further, the dispersion of the second monochromator becomes twice as large as that of the first monochromator. Since the first monochromator can also be used as a prepositional monochromator whose main object is to eliminate the stray light, it may be effective to use a grating with a smaller dispersion for the first monochromator.

As described above, according to this invention, through the switching between optically series and parallel connections of a plurality of monochromators, the measuring modes of a spectrophotometric analyzer can be changed in a compact fashion.

We claim:
1. A spectrophotometric analyzer comprising:
  a light source;
  first and second monochromators capable of operating independently of each other and each having an entrance slit to which a light beam from said light source is made to be incident, means for scanning wavelength by dispersing said light beam which has entered said entrance slit, and an exit slit through which a light beam coming out from said dispersion/scanning means is issued, said entrance and exit slits of said first monochromator and said entrance and exit slits of said second monochroma- tor being disposed rotation symmetrically with respect to a center axis;

first and second detectors for detecting analyzed light beams from said first and second monochromators respectively;

and a switching means for selecting and setting one of a parallel mode where said first and second monochromators are operated independently for detection and a series mode where the analyzed light beam from said exit slit of said first monochromator is made to be incident on said entrance slit of said second monochromator.

2. A spectrophotometric analyzer according to claim 1, wherein said switching means comprises a first mirror for reflecting the analyzed light beam from said exit slit of said first monochromator, a second mirror for reflecting the light beam reflected from said first mirror and making it incident on said entrance slit of said second monochromator, and slide means for holding said first and second mirrors and for sliding between a first position for providing said parallel mode and a second position for providing said series mode.

3. A spectrophotometric analyzer according to claim 2, wherein said switching means further comprises means for focussing the image of said exit slit of said first monochromator onto said entrance slit of said second monochromator.

4. A spectrophotometric analyzer according to claim 1, 2 or 3, wherein said dispersion/scanning means includes a grating as a dispersion element.

5. A spectrophotometric analyzer according to claim 4, wherein the grating constants of said gratings in said first and second monochromators are different from each other.

6. A spectrophotometric analyzer according to claim 5, wherein said grating of said first monochromator has a smaller dispersion than that of the grating of said second monochromator.

7. A spectrophotometric analyzer according to claim 1, 2 or 3, wherein said first and second monochromators are arranged so that the incident light beams to said entrance slits and the issued light beams from said exit slits extend in substantially vertical directions.

* * * * *